United States Patent [19]

Coates et al.

[11] Patent Number: 4,487,830

[45] Date of Patent: Dec. 11, 1984

[54] ENZYME/IMMUNOFLUORESCENT ASSAY FOR AUTOANTIBODIES

[75] Inventors: Stephen R. Coates, Leucadia; Walter L. Binder, San Diego, both of Calif.

[73] Assignee: American Hoechst Corporation, Somerville, N.J.

[21] Appl. No.: 378,290

[22] Filed: May 14, 1982

[51] Int. Cl.$^3$ .................. G01N 33/54; C12Q 1/28
[52] U.S. Cl. ........................................ 435/7; 435/28; 436/506; 436/508; 436/509; 436/519
[58] Field of Search ............... 435/7, 28; 436/506, 436/507, 508, 509, 519

[56] References Cited

U.S. PATENT DOCUMENTS 4,144,031  3/1979  Acevedo et al. .................. 436/818

FOREIGN PATENT DOCUMENTS

W083/00877  3/1983  PCT Int'l Appl. .
2067286  7/1981  United Kingdom .

*Primary Examiner*—Blondel Hazel
*Attorney, Agent, or Firm*—James R. Cartiglia; Natalie Jensen

[57] ABSTRACT

A method for the determination of autoantibody in a test sample comprises contacting a substrate for the autoantibody with sample; treating the contacted substrate with labeled antihuman antibody selected from (1) a mixture comprising enzyme labeled antihuman antibody and fluorescent labeled antihuman antibody, and (2) antihuman antibody labeled with an enzyme and a fluorescent label; determining the enzyme activity of the treated substrate; and determining the immunofluorescent patterns in substrates exhibiting enzyme activity. The method is useful for the rapid screening and characterization of autoantibodies.

9 Claims, No Drawings

ENZYME/IMMUNOFLUORESCENT ASSAY FOR AUTOANTIBODIES

BACKGROUND OF THE INVENTION

Immunofluorescence is routinely employed in testing human serum for the presence of autoantibodies associated with various disease states. The immunofluorescent antibody technique consists of two antigen—antibody reactions. The first reaction takes place between autoantibody contained in the serum sample and specific antigen localized in a particular substrate. The second reaction is between the autoantibody/antigen complex and antihuman antibody that has been tagged with a fluorescent label. After the second reaction, the substrate is examined for fluorescence using the fluorescent microscope. In positive samples, the patterns of fluorescence are used as indicators for additional tests.

In spite of its accuracy and ease of use, the immunofluorescent antibody technique has one major disadvantage. It does not allow for quick screening of a number of serum samples since each sample must be individually studied under a fluorescent microscope to ascertain whether the serum is positive or negative. Since the majority of sera routinely tested are negative for autoantibody, the advantages of a method which would eliminate microscopic examination of negative sera are obvious. Such a method would be less labor intensive and therefore less expensive.

It is an object of the present invention to provide a fast and accurate method of screening a large number of serum samples for autoantibody, which, when present, can be immediately characterized as to autoantibody type by fluorescent microscopy.

SUMMARY OF THE INVENTION

The present invention relates to a method for the determination of autoantibodies. More particularly, the invention relates to a single assay method that can be used to screen test samples for the presence of autoantibody and characterize detected autoantibody as to type. The unique feature of the method of the present invention resides in tagging the complex of autoantibody and specific antigen with both an enzyme label and a fluorescent label. It is this dual labeling that enables the assay method to be used for both detection and characterization of autoantibodies.

In summary, the present invention relates to a method for the determination of autoantibody in a test sample, comprising:
 providing a substrate for said autoantibody;
 contacting said substrate with test sample;
 treating said contacted substrate with labeled antihuman antibody, said labeled antihuman antibody selected from the group consisting of:
  (1) a mixture comprising enzyme labeled antihuman antibody and fluorescent labeled antihuman antibody; and
  (2) antihuman antibody labeled with an enzyme and a fluorescent label;
 determining the enzyme activity of the treated substrate; and
 determining the immunofluorescent pattern of substrates exhibiting enzyme activity.

A first preferred aspect of the present invention relates to that embodiment wherein the labeled antihuman antibody is a mixture comprising enzyme labeled antihuman antibody and fluorescent labeled antihuman antibody.

A second preferred aspect of the present invention relates to that embodiment wherein the labeled antihuman antibody is antihuman antibody labeled with an enzyme and a fluorescent label.

DETAILED DESCRIPTION

Antibodies determined by the method of the present invention are formed in response to, and react against a subject's own normal, endogenous body constituents. Such antibodies are termed autoantibodies. The following table summarizes the clinical significance of representative autoantibodies that can be determined according to the present invention.

| Autoantibody | Clinical Significance |
| --- | --- |
| Antinuclear antibody (ANA) | Various collagen diseases, aging processes and malignancies. High titer, systemic lupus erythematosus. Drug induced, mixed connective tissue disease. |
| Antimitochondrial antibody(AMA) | High titer, primary biliary cirrhosis; low titer, non-specific immunologic disturbances. |
| Antismooth muscle antibody | Chronic active hepatitis, lupoid hepatitis, primary biliary cirrhosis, viral infections. |
| Antiparietal cell antibody | Pernicious anemia, atopic gastritis. |
| Antithyroid Antibody | High titer, early Hashimoto's thyroiditis and exophthalmic goiter; low titer, primary myxedema. |
| Anti-islet cell Antibody | Insulin dependent diabetes (Type II) |
| Antiadrenal Antibody | Addisons disease |

The detection and quantitation of autoantibodies according to the present invention is accomplished by contacting a suitable antigen substrate with test specimen; treating the contacted substrate with labeled antihuman antibody, said labeled antibody selected from the group consisting of (1) a mixture comprising enzyme labeled antibody and fluorescent labeled antibody and (2) antihuman antibody labeled with an enzyme and a fluorescent label; determining the enzyme activity of the treated substrate; and determining the immunofluorescent pattern of substrates exhibiting enzyme activity.

Substrates suitable for use in the present invention include tissue sections, cells, cell monolayers, sub-cellular components and the like. The substrate contains the antigen used to determine the presence of autoantibody in the test specimen. For best results, it is advisable that the tissue section or other substrate material containing the antigen be prepared in such a way as to preserve antigenic determinants. This means that fixatives are best avoided, or used only with caution.

Examples of cell lines that can be used as sources of antigen in the present invention include, for example, human larynx epidermoid carcinoma cells (Hep-2, ATCC CCL 23), human oral epidermoid carcinoma cells (KB, ATCC CCL 17), human amnion cells (WISH, ATCC CCL 25) and Syrian or Golden hamster kidney cells (BHK-21(C-13), ATCC CCL 10).

Examples of tissue sections that can be used as sources of antigen for the determination of autoantibodies according to the present invention include, for example, mouse and rat kidney, liver and stomach and monkey thyroid, skin and adrenal glands.

The antigen substrate utilized will depend on the type of autoantibody under investigation. For example, the determination of antismooth muscle antibody requires an antigen substrate that contains smooth muscle. Similarly, the determination of antiparietal cell antibody, antithyroid antibody, anti-islet cell antibody and antiadrenal antibody requires antigen substrates that contain gastric parietal cells, thyroid cells, pancreas islet cells and adrenal cells, respectively.

Substrates utilized herein are preferably supported on flat, transparent surfaces to facilitate the determination of immunofluorescent patterns. Particularly suitable support surfaces are afforded by tissue culture treated microtiter plates. Such plates preferably have a well bottom thickness of less than 0.5 mm which allows one to use high magnification objectives in examining the substrate.

Labeled antihuman antibody, used to tag the complex of autoantibody and substrate antigen, is selected from one of the following categories:

(1) a mixture comprising enzyme labeled antihuman antibody and fluorescent labeled antihuman antibody; and (2) antihuman antibody labeled with an enzyme and a fluorescent label.

Fluorochrome conjugated antisera, utilized as fluorescent labeled antihuman antibody herein, are available commercially or may be prepared by the method of M. Goldman described in Fluorescent Antibody Methods 101, (1968), Academic Press Inc., New York. Commercially available fluorochrome conjugated antisera that may be utilized in the present invention include fluorescein and rhodamine conjugated antisera.

Enzyme conjugated antisera, utilized as enzyme labeled antihuman antibody herein, are available commercially or may be readily prepared by methods well known in the art. Enzymes that are particularly preferred as labeling agents include, for example, horseradish peroxidase, alkaline phosphatase, glucose oxidase, lactoperoxidase and $\beta$-galactosidase.

In an alternative mode, antihuman antibody labeled with both an enzyme and a fluorescent label is used in lieu of a mixture comprising enzyme labeled antihuman antibody and fluorescent labeled antihuman antibody. Fluorochrome/enzyme conjugated antisera are readily prepared by reacting a commercially available enzyme/fluorochrome conjugate with a suitably purified immunoglobulin fraction.

In practicing the method of the present invention, antigen substrate, test sample suspected of containing autoantibody and labeled antihuman antibody are combined and handled as discussed below.

Antigen substrate for the autoantibody under investigation is contacted at room temperature with test sample suspected of containing the autoantibody. The period of contact is from 30 minutes to one hour. If the test sample contains autoantibody specific for the antigen localized in the substrate, a substrate bound autoantibody/antigen complex is formed. After repeated washings, the contacted substrate is treated with labeled antihuman antibody selected from the group consisting of (1) a mixture comprising enzyme labeled autihuman antibody and fluorescent labeled antihuman antibody, and (2) antihuman antibody labeled with an enzyme and a fluorescent label. Treatment of the substrate with labeled antibody is carried out at room temperature a period of 30 minutes to one hour. If the treated substrate contains bound autoantibody, a labeled substrate is formed at this stage. After repeated washings, the enzyme activity of the substrate is determined by the addition of a specific substrate for the enzyme. A variety of substrates suitable for enzymes recited and employed herein can be found in Bergmeyer, Methods of Enzymatic Analysis, Academic Press, New York, 1965.

The presence of enzyme activity in the substrate can be determined visually and spectrophotometrically. In the first instance, the substrate is simply examined visually for color produced by the enzymatic cleavage of the enzyme substrate (chromogen). In the second instance, the O.D. of the chromogen solution is determined and correlated with autoantibody titer which is an estimation of the amount of autoantibody in the test sample. Thus, the use of an enzyme label in the method of the present invention allows the method to be employed as either a qualitative or quantitative test for the determination of autoantibody.

Test samples which exhibit enzymatic activity are further characterized by direct examination using a fluorescent microscope to determine the immunofluorescent pattern.

The type of autoantibody bound by the substrate antigen is determined by observing the specific immunofluorescent pattern. For example, fluorescent staining of the nucleus is considered specific for antinuclear antibodies (ANA). ANA patterns are classified as homogeneous (a uniform, solid fluorescent stain throughout the nucleus); peripheral or rim (fluorescent staining of the rim or edge of the nucleus), nucleolar (fluorescent staining of the nucleolus) and speckled (numerous, discrete specks of fluorescent staining throughout the nucleus). The homogeneous pattern is non-specific in that a number of diseases could be indicated, however it has recently been reported that the nucleolar pattern, peripheral or rim pattern and speckled pattern are indicative of scleroderma, systemic lupus erythematosis and mixed connective tissue disease respectively. Fluorescent staining of the mitochondria is considered specific for antimitochondrial antibodies which are indicative of primary biliary cirrhosis (high titer) and non-specific immunologic disturbances (low titer). Fluorescent staining of the smooth muscle of blood vessels contained in the substrate is specific for anti-smooth muscle antibodies. The presence of antismooth muscle antibody is indicative of chronic active hepatitis, lupoid hepatitis or primary biliary cirrhosis. The presence of antismooth muscle antibody may also be indicative of a viral infection.

The terms "test sample" and "test specimen" as used herein refer to autoantibody containing fluids such as human serum and human plasma.

Specific fluorescent staining of parietal cells, thyroid cells, pancreas islet cells and adrenal cells is indicative of the disease states previously discussed on pages 5 and 6.

DESCRIPTION OF SPECIFIC EMBODIMENTS

The following specific description is given to enable those skilled in the art to more clearly understand and practice the invention. It should not be considered as a limitation upon the scope of the invention but merely as being illustrative and representative thereof.

EXAMPLE I

The cells utilized in the substrate of the present example are human larynx epidermoid carcinoma cells (Hep-2, ATCC CCL 23) obtained from the American Type Culture Collection, Rockville, Md.

The Hep-2 cells are harvested from a 75 cm$^2$ flat surfaced flask grown to confluency. After rinsing the flask with phosphate buffered saline, cell detachment is accomplished using 5 ml of 0.05% trypsin and 0.02% EDTA (ethylene-diamine-tetraacetic acid). Trypsinization is halted by adding to the cell suspension 200 ml of Dulbecco's Modified calf serum and gentamycin (50 µg/ml). A sample of the cell suspension is counted with a hemocytometer to determine the total number of cells present. The cell suspension is then adjusted to a cell concentration of $1.0 \times 10^4$ to $8.0 \times 10^5$ cells/ml by the addition of Eagle's minimum essential medium.

The substrate is prepared by growing Hep-2 cells on a suitable support. Support means employed herein are flat bottom 96 well polystyrene microtiter plates which have been treated to facilitate binding of the cells to the plates. The tissue culture treated microtiter plates are obtained from Dynatech Laboratories, Inc., Alexandria, Va.

Each well of a microtiter plate is filled with 0.2 ml of the above described Hep-2 cell suspension. The plate is then incubated at 37° C. overnight in a 5% CO$_2$ incubator. After incubation, growth medium is removed by suction and the plate is washed twice with phosphate buffered saline, pH 7.0. The cell monolayer contained in each well is then fixed by adding 0.2 ml of cold methanol (4° C.) to each well followed by incubation of the plate at room temperature. After 15 minutes, methanol is removed from the wells and the plate is dried prior to use.

EXAMPLE II

Materials

I. Buffer: 0.05 M Tris buffered saline, pH 7.2, containing 4% Tween 20 and 1% agamma calf serum.
II. Fluorescein-antihuman IgG(H+L) conjugate solution: Miles Laboratories, Code No. 65-169-2.
III. Horseradish peroxidase—antihuman IgG(H+L) conjugate solution: Miles Laboratories, Code No. 61-231-1.

One ml of fluorescein-antihuman IgG conjugate solution (65-169-2) and one ml of horseradish peroxidase-antihuman IgG conjugate solution (61-231-1) are each serially diluted with buffer to provide conjugate dilutions of ⅛, 1/16, 1/32, 1/64 and 1/250, 1/500 and 1/1000 respectively. Two-fold serial dilutions of positive and negative test sera for ANA antibody are titrated with the conjugate dilutions. For both conjugates, the optimum use concentration is that dilution which exhibits a negative reaction with negative test specimen and the highest allowable sensitivity with positive test specimen. The optimum use concentration for the fluorescein-antihuman IgG conjugate is a dilution of 32. The optimum use concentration for the horseradish peroxidase-antihuman IgG conjugate is a dilution of 500.

Based on the above stated optimum use concentrations, 300 µl of fluorescein-antihuman IgG conjugate solution is added to 4.5 ml of buffer and 200 µl of horseradish peroxidase-antihuman IgG conjugate solution is added to 5 ml of buffer. The resulting solutions are then combined to afford a buffered solution of fluorescein labeled antihuman IgG and horseradish peroxidase labeled antihuman IgG. The solution is stored at 4° C. prior to use.

EXAMPLE III

Materials

I. Fluorescein-horseradish peroxidase conjugate: FITC-peroxidase (Code No. P2649) obtained from Sigma Chemical Company, Saint Louis, Mo.
II. Goat antihuman IgG(H+L): Code No. 8428-13 obtained from Bionetics Laboratory Products, Kensington, Md.

Ten milligrams of FITC-peroxidase (P 2649) is dissolved in 0.2 ml phosphate buffered saline, pH 6.8, containing 1.25% glutaraldehyde. The mixture is allowed to stand overnight at room temperature and is then dialyzed against normal saline to remove free glutaraldehyde. The resulting FITC-peroxidase solution is made up to 1.0 ml in normal saline.

The goat antihuman IgG solution is adjusted to 5 mg/ml with normal saline. Protein concentration of the globulin solution is determined by the method of Lowry et al, J. Biol. Chem. 193:265–275(1951).

One ml of the globulin solution is mixed with 1.0 ml of the FITC-peroxidase solution. Thereafter, 0.1 ml 1M carbonate bicarbonate buffer, pH 9.5, is added and the mixture is allowed to stand at 4° C. After 24 hours, 0.1 ml 0.2 M lysine solution is added and the mixture is kept at room temperature. After 2 hours, the mixture is dialyzed overnight against phosphate buffered saline, pH 7.2. Fluorescein-horseradish peroxidase labeled antihuman IgG is precipitated from solution by the addition of an equal volume of saturated ammonium sulfate solution. The precipitate is washed twice in saturated ammonium sulfate and then suspended in 1.0 ml phosphate buffered saline. The conjugate is dialyzed against phosphate buffered saline extensively and then centrifuged at $10,000 \times g$ for 30 minutes and the sediment discarded. Bovine serum albumin is then added to 1%. The resulting fluorescein-horseradish peroxidase labeled antihuman IgG solution is then filtered through a Millipore filter (0.22 µm) and stored at −20° C., or at 4° C. when an equal amount of glycerol is added.

EXAMPLE IV

Hep-2 cells attached to wells of a microtiter plate according to the method of EXAMPLE I are employed to determine the presence and amount of antinuclear antibody (ANA) in human sera according to the procedure described infra.

Each well of a microtiter place, prepared as described in EXAMPLE I, is filled with 0.2 ml of 0.05 M Tris buffered saline containing 1% agamma calf serum and 4% Tween 20 (polyoxyethylene sorbitan monolaurate). Thereafter, 20 µl of each test specimen, 20 µl of ANA positive control and 20 µl of ANA negative control are added to separate wells and the well contents are then mixed by gently tapping the plate against a hard surface. The plate is incubated at room temperature. After 2 hours, the well contents are removed by suction and the plate is washed three times by the addition and subsequent removal of 0.05 M Tris buffered saline containing 1% Tween 20.

After the final wash, 0.1 ml of the buffered solution of fluorescein labeled antihuman IgG and horseradish peroxidase (HRP) labeled antihuman IgG, prepared according to the method of EXAMPLE II, is added to each well. Thereafter, the plate is incubated at room temperature. After 2 hours, the well contents are removed by suction and the plate is then washed three times with 0.05 M Tris buffered saline containing 1% Tween 20.

After the final wash, 0.1 ml of substrate-chromogen solution is added to each well. The solution is prepared by mixing one volume of 0.0025 M 4-aminoantipyrine containing 0.17 M phenol with an equal volume 0.0017 M $H_2O_2$ in 0.2 M $PO_4$ buffer, pH 7.0. Following a 45 minute incubation at room temperature, the HRP catalyzed reaction is stopped by the addition of 0.1 ml of 1% $NaN_3$ to each well. The absorbance of the solution in each well is then measured at 510 nm. The absorbance is proportional to the amount of ANA present. All wells exhibiting a positive absorbance (i.e. an O.D. of at least 0.3) are examined under a fluorescent microscope. Examination is preferably carried out using an inverted fluorescent microscope. Alternatively, a regular fluorescent microscope can be used if the wells of a plate are sealed prior to inverting and examining the plate. The presence of ANA is demonstrated by fluorescent staining of the nuclei of Hep-2 cells in the substrate.

EXAMPLE V

Hep-2 cells attached to wells of a microtiter plate according to the method of EXAMPLE I are employed to determine the presence and amount of antinuclear antibody (ANA) in human sera according to the procedure as described infra.

Each well of a microtiter plate, prepared as described in EXAMPLE I, is filled with 0.2 ml of 0.05 M Tris buffered saline containing 1% agamma calf serum and 4% Tween 20(polyoxyethylene sorbitan monolaurate). Thereafter, 20 $\mu$l of each test specimen, 20 $\mu$l of ANA positive control and 20 $\mu$l of ANA negative control are added to separate wells and the well contents are then mixed by gently tapping the plate against a hard surface. The plate is incubated at room temperature. After 2 hours, the well contents of the plate are removed by suction and the plate is washed three times by the addition and subsequent removal of 0.05 M Tris buffered saline containing 1% Tween 20.

After the final wash, 0.1 ml of the buffered solution of fluorescein-horseradish peroxidase labeled antihuman IgG, prepared according to the method of EXAMPLE III, is added to each well. Thereafter, the plate is incubated at room temperature. After 2 hours, the well contents are removed by suction and the plate is then washed three times with 0.05 M Tris buffered saline containing 1% Tween 20.

After the final wash, 0.1 ml of substrate-chromogen solution is added to each well. The solution is identical to that employed in EXAMPLE IV. Following a 45 minute incubation at room temperature, the HRP catalyzed reaction is stopped by the addition of 0.1 ml of 1% $NaN_3$ to each well. The absorbance of the solution in each well is then measured at 5.0 nm. The absorbance is proportional to the amount of ANA present. All wells exhibiting a positive absorbance (i.e., and O.D. of at least 0.3) are examined under a fluorescent microscope. Examination is preferably carried out using an inverted fluorescent microscope. Alternatively, a regular fluorescent microscope can be used if the wells of the plate are sealed prior to inverting and examining the plate. The presence of ANA is demonstrated by fluorescent staining of the nuclei of Hep-2 cells in the substrate.

What is claimed is:

1. A method for the determination of autoantibody in a test sample, comprising:
   providing a substrate for said autoantibody;
   contacting said substrate with test sample;
   treating said contacted substrate with labeled antihuman antibody, said labeled antihuman antibody selected from the group consisting of:
   (1) a mixture comprising enzyme labeled antihuman antibody and fluorescent labeled antihuman antibody; and
   (2) antihuman antibody labeled with an enzyme and a fluorescent label;
   determining the enzyme activity of the treated substrate; and
   determining the immunofluorescent pattern in substrates exhibiting enzyme activity.

2. A method according to claim 1 wherein said labeled antihuman antibody is a mixture comprising enzyme labeled antihuman antibody and fluorescent labeled antihuman antibody.

3. A method according to claim 1 wherein said labeled antihuman antibody is antihuman antibody labeled with an enzyme and a fluorescent label.

4. A method according to claim 2 or 3 wherein said enzyme is horseradish peroxidase.

5. A method according to claim 2 or 3 wherein said fluorescent label is fluorescein.

6. A method according to claim 2 or 3 wherein said enzyme is horseradish peroxidase and said fluorescent label is fluorescein.

7. A method according to claim 6 wherein said autoantibody comprises antinuclear antibodies.

8. A method according to claim 7 wherein said antihuman antibody is antihuman IgG.

9. A method according to claim 8 wherein said substrate comprises Hep-2 cells.

* * * * *